United States Patent [19]

Kramer et al.

[11] 4,047,521
[45] Sept. 13, 1977

[54] RATE-OF-FLOW METER, PARTICULARLY FOR DIAGNOSTIC SPIROMETRY

[76] Inventors: Carl Kramer, Am Chorusberg 8, 51 Aachen; Hans-Joachim Gerhardt, Ruhrstrasse 12, 5023 Lovenich, both of Germany

[21] Appl. No.: 628,701

[22] Filed: Nov. 4, 1975

[51] Int. Cl.² .............................................. A61B 5/08
[52] U.S. Cl. .................................. 128/2.08; 73/211; 73/212
[58] Field of Search ............... 128/2.08, 2.07, 2 C; 272/99; 73/211, 212, 205 R

[56] References Cited

U.S. PATENT DOCUMENTS

| 1,110,023 | 9/1914 | Wilkinson | 73/212 |
| 1,438,811 | 12/1922 | Coyne | 73/212 |
| 1,924,125 | 8/1933 | Linderman, Jr. | 73/211 |
| 2,035,472 | 3/1936 | Hammond | 73/211 |
| 2,100,978 | 11/1937 | Rheinlander | 73/211 |
| 3,045,666 | 7/1962 | Dubsky et al. | 128/2.08 |
| 3,312,106 | 4/1967 | Davis | 73/212 |

FOREIGN PATENT DOCUMENTS

| 278,011 | 11/1970 | U.S.S.R. | 128/2.08 |

*Primary Examiner*—Robert W. Michell
*Assistant Examiner*—Lee S. Cohen
*Attorney, Agent, or Firm*—John C. Smith, Jr.

[57] ABSTRACT

A rate-of-flow meter, particularly for diagnostic spirometry, comprises a flow tube containing, on diametrically opposite sides, a measuring stud provided with pressure taps and a displacement body facing the stud.

11 Claims, 12 Drawing Figures

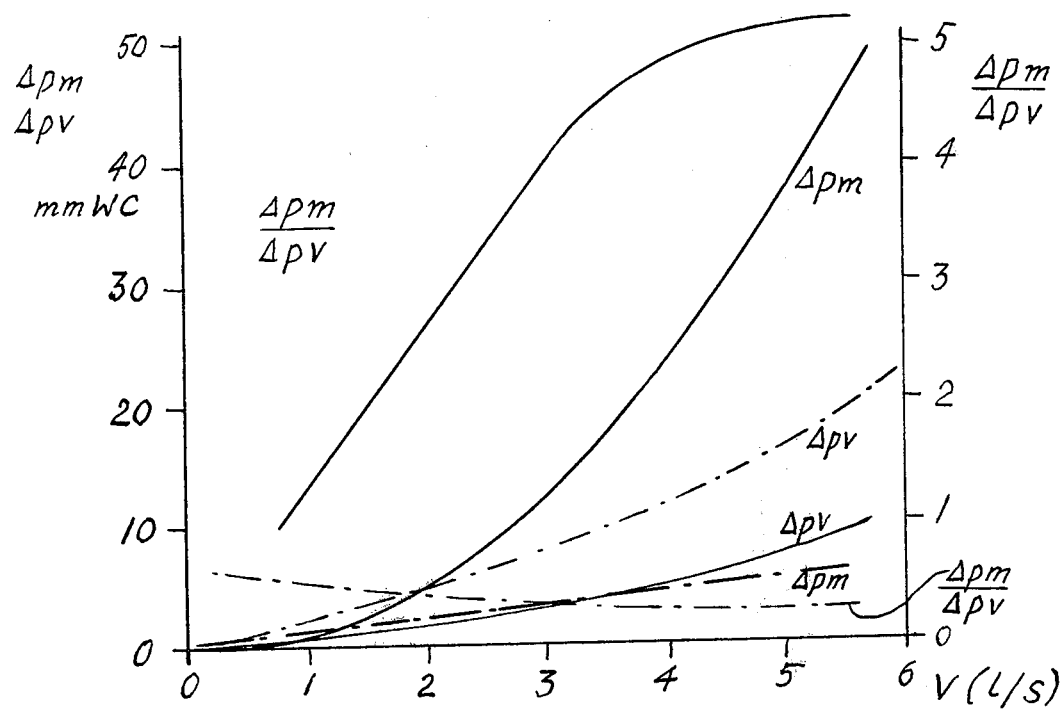
FIG. 1 — · — · — PNEUMOTACHOGRAPH BY FLEISCH
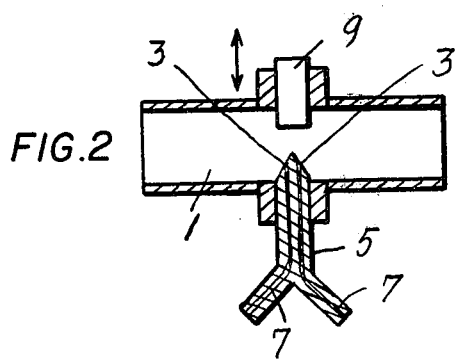
FIG. 2
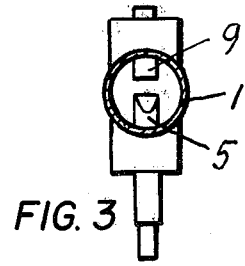
FIG. 3

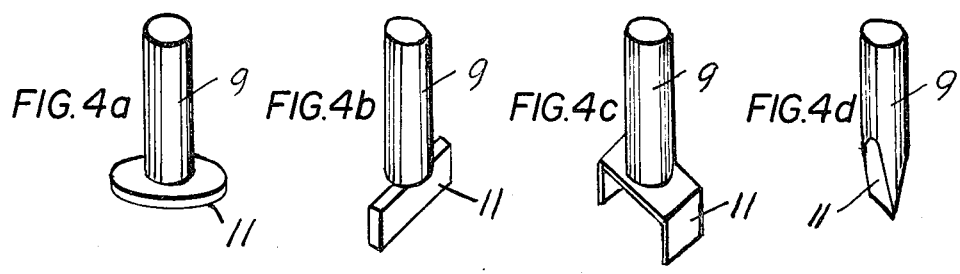
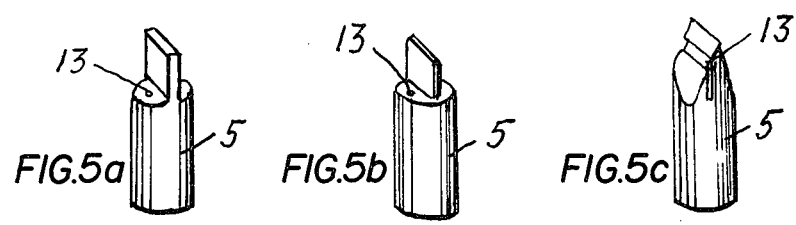
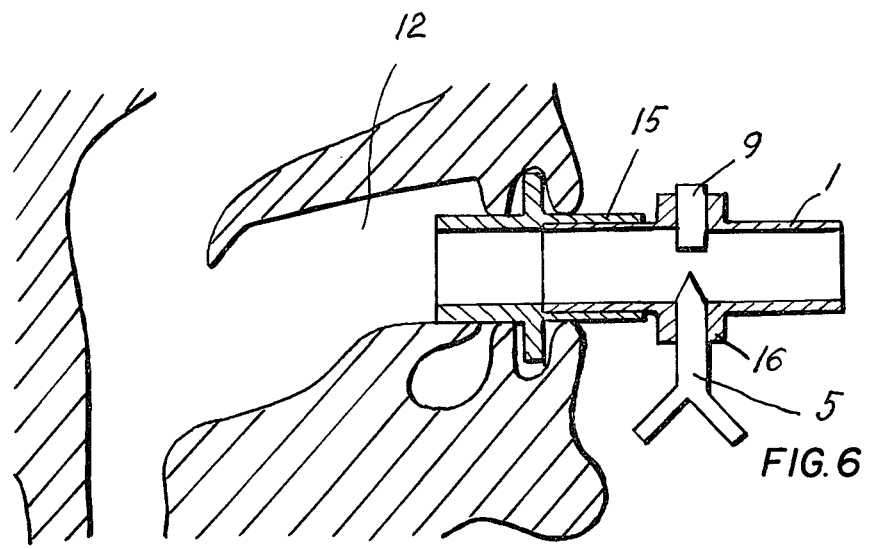
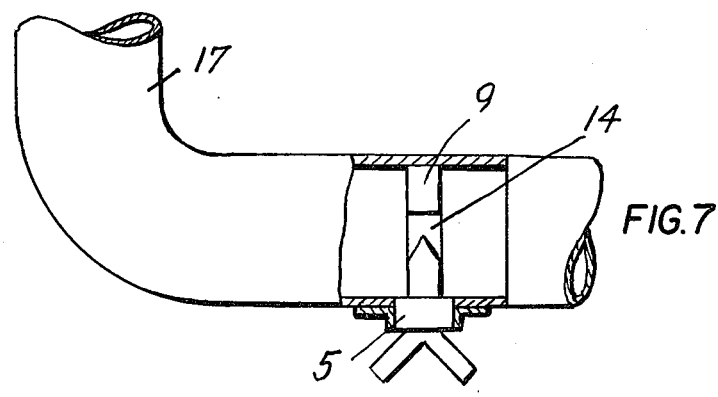

RATE-OF-FLOW METER, PARTICULARLY FOR DIAGNOSTIC SPIROMETRY

BACKGROUND OF THE INVENTION

This invention relates to a rate-of-flow meter, particularly for diagnostic spirometry, containing a measuring stud provided with pressure taps and an adjustable displacement body.

In diagnostic spirometry such rate-of-flow meters are known as pneumotachographs. Well known is the Fleisch pneumotachograph in which a theoretically linear relationship between the measured pressure and the volumetric rate of flow is achieved by maintaining laminar flow through a plurality of parallel vanes of small cross section to create the desired pressure differential between the pressure taps. Objections to this rather complex and expensive instrument are the difficulty of keeping it clean and of disinfecting it, its relatively great weight and the rather poor signal strength that is available for measurement. This signal is provided exclusively by the pressure drop which arises during flow through the large number of parallel passages between the vanes. Any increase in signal strength therefore involves a corresponding increase in flow resistance. In a respiratory examination of the functioning of the lung it is desirable that this resistance should be a minimum. Other difficulties in practice arise because flow through the several channels may not be uniform and particularly because this may differ when the breath is inhaled and when it is expelled. Moreover, the measured pressure differential in laminar flow also depends on the viscosity of the medium. Finally, obstructions for instance by expectorated phlegm when coughing may considerably affect the results of the measurement. Other drawbacks are the relatively large unused capacity which causes errors when examining gas exchange, and the high demands on accuracy which the very small measuring signal makes on the efficiency of the electrical indicating system.

A more recent pneumatometer (German Specification published as-filed under No. 2,044,101) which is based on the same physical principle as the Fleisch pneumotachograph also avails itself of the pressure drop in laminar flow for making the measurement.

Another proposal relating to the design of a pneumatometer (German Specification published as-filed under No. 1,963,349) for generating the measured pressure avails itself of a flat flow resistor which completely fills the cross section of the flow tube. Such a flow resistor may be for instance a fine mesh. However, such resistors have the major disadvantage that the pressure drop they cause, being rendered dimensionally indeterminate by reference to a static pressure, depends in a complicated way upon the Reynold's number, particularly in the case of screens and nets. Consequently in the description of pneumatometers based on this working principle (German Specifications published as-filed under Nos. 1,963,349 and 2,000,800) there is always the qualification that the measuring accuracy that can be achieved is not very high.

Another rate-of-flow meter used in spirometry comprises two pitot tubes concentrically inserted in a breathing tube and operating in contrary directions, the static heads in each being applied to a differential pressure gauge (German Specification published as-filed under No. 1,153,486). In this arrangement the pitot tube which faces the direction of flow provides the total head whereas that pointing in the direction of flow approximately represents the static head. In order of magnitude the pressure difference therefore corresponds to the static pressure head. A high static head which would be desirable in the interests of improved measuring accuracy can be achieved only by a fairly considerable constriction of the cross section of the breathing tube. Such a constriction naturally represents an increase in resistance to flow. Consequently the static heads in a breathing tube cannot be very high. A drawback which appears particularly when measuring low rates of flow is the dependence of the pattern of flow through the two pitot tubes upon the Reynold's number. Owing to this effect the relationship between measured pressure and volume rate of flow may considerably deviate from the expected parabolic relationship.

SUMMARY OF THE INVENTION

The main object of the present invention is to provide a rate-of-flow meter which is of uncomplicated design and simple to manufacture, though complying with the demand for a low idle capacity and for low resistance to flow, and which will nevertheless provide a relatively high-strength signal even when the rates of flow of the breath are low.

Another object is to simplify handling of the instrument in practice, and to permit it to be cleaned even during use, whilst at the same time keeping the overall dimensions and its weight low, and giving the patient more freedom of movement during an examination by connecting the flow meter directly to the mouthpiece and/or integrally combining the two components in such a manner that the instrument can be held without needing a stand or other means of support.

The instrument according to the present invention which achieves these objects comprises a simple flow tube into which a measuring stud containing pressure taps projects radially from one side and faces a displacement body on the other side. This combination of a measuring stud with a displacement body generates the high velocity of flow which is necessary for achieving a relatively high pressure differential, but at the same time it localises the zone of high velocity within a small part of the tube cross section. The proposed arrangement thus enables pressure differentials to be achieved which considerably exceed the static pressure in the breathing tube.

BRIEF DESCRIPTION OF THE DRAWINGS

Some preferred embodiments of the invention will now be described by way of example and with reference to the accompanying drawings, in which:

FIG. 1 shows the results of comparative measurements achieved by the rate-of-flow meter according to the invention and by the known Fleisch pneumotachograph;

FIG. 2 is a longitudinal section of the rate-of-flow meter;

FIG. 3 is a cross section thereof;

FIGS. 4a, 4b, 4c and 4d show a variety of different forms of construction of the displacement body;

FIGS. 5a, 5b and 5c illustrate various forms of construction of the measuring stud;

FIG. 6 is a cross section of an arrangement in which the flow tube is directly attached to a mouthpiece, and FIG. 7 shows another embodiment in which the displacement body and the measuring stud are combined to form a unit.

DESCRIPTION OF THE PREFERRED EMBODIMENTS

In FIG. 1 the measured pressure head $\Delta pm$, the pressure drop $\Delta pv$ and the ratio of pressure drop to measured pressure head are plotted for each instrument over the rate of flow V. The same hook-up arrangements were used for both rate-of-flow meters, corresponding to those normally employed for instance in a conventional plethysmograph chamber. In other words allowance has been made for the pressure drop in mouthpiece and pipes. The pneumotachograph according to Fleisch was of a standard type available on the open market. The absolute value of the pressure drop is substantially lower throughout the range of flow rates in a rate-of-flow meter according to the invention than in a pneumotachograph according to Fleisch. Consequently the curve representing the plot over the rate of flow of the ratios of pressure loss and measured pressure differential is also much better than formerly.

The rate-of-flow meter according to the invention is shown in FIG. 2 and FIG. 3 and comprises a flow tube 1. The measured pressures are tapped at pressure taps 3 in the end of a measuring stud 5 and are transmitted through channels 7 and lengths of hose to a differential pressure gauge. The slidable adjustability of a displacement body 9 in direction of its axis—in FIGS. 2 and 3 the body 9 is a simple cylinder—is indicated in FIG. 2 by a double-headed arrow. By appropriate displacement the magnitude of the increase in the velocity of flow in the neighborhood of the head of the measuring stud 5 can be varied in a defined way and the sensitivity of the flow meter easily varied. The proposed combination of a measuring stud 5 with a displacement body 9 also ensures that the velocity distribution over the cross section of the tube 1 has no perceptible effect on the result of the measurement. The change in the velocity distribution due to the presence of the measuring stud 5 and of the displacement body 9 in the neighborhood of the pressure taps 3 is considerable compared with the variations in the cross sectional velocity distribution in the rest of the tube, such as may arise under varying practical circumstances when the entry conditions into the tube 1 vary. This effect and the knife edge design of the ends of the measuring stud 5 and of the displacement body 9 causes the pressure differential which is measured by the proposed rate-of-flow meter in non-dimensional form to be substantially independent of the Reynold's number. The theoretically expected parabolic relationship between pressure differential and rate of flow is therefore substantially achieved. This is of importance for a subsequent electronic linearisation of the electrically amplified signal.

For the purpose of further reducing the overall pressure loss the flow tube 1 may have a cylindrical centre portion containing the measuring stud 5 and the displacement body 9 and a divergent portion at each end, like a Venturi, so that the greater part of the energy of motion in the throat of the tube is recoverable in pressure form.

FIGS. 4a – d illustrate a variety of different forms of construction of the displacement body 9. Their common feature is the sharply angled knife edge which may be of arcuate, angular or off-angled shape, at the end 11 of the displacement body facing the measuring stud 5.

The end 11 of the displacement body may be a thin sheet metal plate which laterally embraces the measuring stud 5 (FIG. 4c). The displacement body may consist of a solid bar material of circular or polygonal cross-sectional. FIGS. 5a, 5b and 5c illustrate various forms of construction of the measuring stud. Their common feature is that below its upper edge (viewed as illustrated in FIGS. 5a, 5b and 5c the stud contains two symmetrically disposed pressure taps 13. The upper edge of the measuring stud is also sharp edged. This edge may also be formed by a sheet metal plate (FIG. 5b) let into the upper end of the stud between the two orifices of the pressure taps 13. Moreover, as illustrated in FIG. 5c these orifices 13 may be slots and the entries into the bores may be secreted. This will be particularly desirable when it is possible for the pressure taps to be blocked or obstructed by contamination with particles of phlegm or the like. The measuring stud 5 is fitted into the flow tube so that the line connecting the orifices 13 of the pressure taps is parallel to the tube axis. The width of the displacement body normal to the axis of the flow tube may be at least equal to the corresponding width of the measuring stud.

In order to reduce the unwanted idle capacity of the flow tube 1 it may be directly attached to a mouthpiece 15. A rate-of-flow meter 16 of this kind is schematically illustrated in FIG. 6. The mouthpiece is shown pushed into the patient's mouth 12.

In order to prevent the formation of condensate at the measuring stud 5 and on the displacement body 9 the flow tube 1 may be electrically heated, for instance by means of a resistance wire.

For industrial applications, for instance for rate-of-flow measurements in pipes or as a sensor in control systems, the displacement body 9 and the measuring stud 5 may also be integrally combined so that both can be conveniently fitted as a unit into an existing pipe line 17, as illustrated in FIG. 7. By suitably matching the dimensions of the stud and of the displacement body to the diameter of the pipe it is possible for calibration curves to be applicable to different sized ducts and pipes, so that special calibration can be dispensed with. The measuring stud 5 and the displacement body 9 may be contained in a common holder 14.

The invention may be embodied in other specific forms without departing from the spirit or essential characteristics thereof. The embodiments are therefore to be considered in all respects as illustrative and not restrictive.

What is claimed is:

1. A rate-of-flow meter, particularly for diagnostic spirometry, comprising:
   a. wall means defining a flow tube extending along an axis for conducting a gas therethrough;
   b. a measuring stud and a displacement body, each extending radially of said axis through said wall means from the exterior to the interior of said flow tube, said measuring stud and displacement body passing through said wall means at diametrically opposite sides of said flow tube such that the respective ends of said measuring stud and displacement body are in spaced confronting relationship, the space therebetween being substantially less than the interior cross-sectional width of said flow tube and the cross-sectional widths of said measuring stud and displacement body being substantially less than the interior cross-sectional width of said flow tube such that resistance to flow through said flow tube is minimized;
   c. the confronting end of said displacement body terminating in at least one knife edge, and the confronting end of said measuring stud terminating in a longitudinally extending knife edge oriented in a direction substantially perpendicular to said axis;

d. at least two symmetrically disposed orifices in said measuring stud at opposite sides of said longitudinally extending edge respectively and ducts extending through said measuring stud from said orifices for transmitting the pressure differential on opposite sides of said edge of said measuring studs; and e. means for displacing one of said displacement body and measuring stud relative to the other in a direction normal to said axis whereby the magnitude of the increase in velocity of flow between said end of said measuring stud and said end of said displacement body can be varied.

2. A rate-of-flow meter as defined in claim 1, including means for displacing the body in the radial direction of the tube for the purpose of varying the measuring sensitivity of the rate-of-flow meter.

3. A rate-of-flow meter as defined in claim 1, wherein the displacement body consists of solid bar material of circular cross section provided with a sharp edge at its end facing the measuring stud.

4. A rate-of-flow meter as defined in claim 1, wherein the displacement body consists of solid bar material provided with a sharp edge at its end facing the measuring stud.

5. A rate-of-flow meter as defined in claim 1, wherein the end of the displacement body facing the stud carries a sheet metal plate having a sharp edge of arcuate shape.

6. A rate-of-flow meter as defined in claim 1, further comprising means for adjusting the measuring stud in the radial direction of the flow tube.

7. A rate-of-flow meter as defined in claim 1, further comprising recesses in said measuring stud at opposite sides of said longitudinally extending edge, said orifices being secreted in said recesses.

8. A rate-of-flow meter as defined in claim 1, wherein the width of the displacement body normal to the axis of the flow tube is at least equal to the corresponding width of the measuring stud.

9. A rate-of-flow meter as defined in claim 1, wherein the end of the displacement body facing the stud carries a sheet metal plate having a sharp edge of angular shape.

10. A rate-of-flow meter as defined in claim 1, wherein the end of the displacement body facing the stud carries a sheet metal plate having a sharp edge of off-angled shape.

11. A rate-of-flow meter comprising:

a. wall means defining a flow tube extending along an axis for conducting a gas therethrough;

b. a measuring stud and a displacement body forming an integral unit and means for releasably securing said integral unit in said flow tube;

c. said measuring stud and displacement body being located, when said integral unit is secured in said flow tube, at diametrically opposite sides of said flow tube such that the respective ends of said measuring stud and displacement body are in spaced confronting relationship, the space therebetween being substantially less than the interior cross-sectional width of said flow tube and the cross-sectional widths of said measuring stud and displacement body being substantially less than the interior cross-sectional width of said flow tube such that resistance to flow through said flow tube is minimized;

d. the confronting end of said displacement body terminating in at least one knife edge, and the confronting end of said measuring stud terminating in a longitudinally extending knife edge oriented in a direction substantially perpendicular to said axis; and e. at least two symmetrically disposed orifices in said measuring stud at opposite sides of said longitudinally extending edge respectively and ducts extending through said measuring stud from said orifices for transmitting the pressure differential on opposite sides of said edge of said measuring stud.

* * * * *